United States Patent [19]
Ciobanu et al.

[11] Patent Number: 5,970,801
[45] Date of Patent: Oct. 26, 1999

[54] VARIABLE ORIFICE FLOW SENSOR

[75] Inventors: Calin Ion Ciobanu, Brea; Donald Schaeffer, Riverside, both of Calif.

[73] Assignee: Bear Medical Systems, Inc., Waltham, Mass.

[21] Appl. No.: 08/994,501

[22] Filed: Dec. 30, 1997

[51] Int. Cl.⁶ ............................... G01F 1/37; G01F 1/22
[52] U.S. Cl. ..................... 73/861.52; 73/861.53
[58] Field of Search ........................... 73/861.53, 861.52, 73/861.71, 861.73, 861.74, 861.76; 138/43, 45, 46; 236/49; 137/527, 630.16; 604/247

[56] References Cited

U.S. PATENT DOCUMENTS

| | | | |
|---|---|---|---|
| 2,899,981 | 8/1959 | Binks ........................................ | 138/46 |
| 2,966,133 | 12/1960 | Hube ........................................ | 116/117 |
| 3,134,404 | 5/1964 | Ziccardi ............................... | 137/925.31 |
| 3,370,305 | 2/1968 | Goott et al. ...................................... | 3/1 |
| 3,460,168 | 8/1969 | Bruyne ........................................ | 4/189 |
| 3,541,945 | 11/1970 | Wexler ..................................... | 98/119 |
| 3,613,720 | 10/1971 | Welch ..................................... | 137/527 |
| 3,857,277 | 12/1974 | Moore ......................................... | 73/28 |
| 3,891,000 | 6/1975 | Melnick ............................... | 135/525.3 |
| 3,971,253 | 7/1976 | Hini et al. ................................. | 73/228 |
| 3,995,661 | 12/1976 | Van Fossen .............................. | 137/807 |
| 4,394,958 | 7/1983 | Whitney et al. ........................... | 236/49 |
| 4,454,768 | 6/1984 | Nansel ................................. | 73/861.76 |
| 4,456,016 | 6/1984 | Nowacki et al. ....................... | 128/725 |
| 4,538,620 | 9/1985 | Nowacki et al. ....................... | 128/725 |
| 4,605,408 | 8/1986 | Carpentier .................................. | 623/2 |
| 4,729,244 | 3/1988 | Furuse ................................ | 73/861.47 |
| 4,874,012 | 10/1989 | Velie ........................................ | 137/557 |
| 4,989,456 | 2/1991 | Stupecky ............................... | 73/863.53 |
| 4,993,269 | 2/1991 | Guillaume et al. .................. | 73/861.53 |
| 5,038,621 | 8/1991 | Stupecky .............................. | 73/861.53 |
| 5,687,767 | 11/1997 | Bowers .................................... | 137/855 |

Primary Examiner—George Dombroske
Assistant Examiner—Robin Clark
Attorney, Agent, or Firm—Stetina Brunda Garred & Brucker

[57] ABSTRACT

A variable orifice flow sensor includes a flow conduit member defining a flow orifice and fluidly connecting first and second fluid flow ports, a flapper of magnetizable sheet metal that is mounted in the conduit member by a hinge portion so that the flapper angularly deflects out of the plane of the orifice in response to fluid flow through the conduit member to vary the effective fluid flow cross-sectional area of the orifice in proportion to the flow rate of fluid through the conduit member, and a pressure sensing tap on either side of the flapper. A deflection-limiting surface is provided in the conduit member adjacent the hinge portion. The hinge portion abuts against the deflection-limiting surface when the flapper experiences an angular deflection at least equal to a predefined angle in response to a fluid flow rate that is at least equal to a predetermined value, whereby overstressing of the hinge portion is minimized. In addition, at least one magnet is provided in the conduit member adjacent the flapper, whereby the magnet generates a magnetic field that acts on the flapper so as to force it into a position that tends to minimize the zero flow gap that exists between the flapper and the portion of the conduit member that defines the fluid flow orifice when there is no fluid flow through the orifice.

34 Claims, 5 Drawing Sheets

VARIABLE ORIFICE FLOW SENSOR

CROSS-REFERENCE TO RELATED APPLICATIONS

Not Applicable

FEDERALLY FUNDED RESEARCH OR DEVELOPMENT

Not Applicable

BACKGROUND OF THE INVENTION

This invention relates generally to the field of fluid flow sensors. More specifically, it relates to improvements in fluid flow sensors of the variable orifice or variable obstruction area type, that are commonly used, in conjunction with a pressure transducer, to generate a differential pressure signal from fluid (especially gas) flow in a conduit, wherein the value of the differential pressure signal is correlated with a flow rate value. The flow rate value, in turn, may be integrated over time to yield a volumetric value.

Flow sensors of the class described above have become commonly used in medical applications, particularly for measuring the flow rate of respiratory gas in medical ventilators. Specific examples of such flow sensors are found in the following U.S. Pat. Nos. 4,989,456—Stupecky; 4,993,269—Guillaume et al.; and 5,038,621—Stupecky. The variable orifice flow sensors exemplified by these patents employ a hinged obstruction or flapper that is mounted within a flow orifice of known area. The flapper is mounted so that the portion of the total area of the orifice that it opens to fluid flow is proportional to the flow rate through the orifice. The pressure drop across the orifice is proportional to the open area through the orifice. Thus, the differential pressure across the orifice is directly related to the flow rate through the orifice. This pressure differential is sensed by pressure ports upstream and downstream from the orifice. The sensed upstream and downstream pressures are directed to a differential pressure transducer, which generates an analog electrical signal having a value representing the differential pressure value. The analog signal is digitized and input to a microprocessor that is programmed to compute a value representing the instantaneous volumetric fluid flow rate through the orifice.

While flow sensors of the type described above have exhibited acceptable levels of accuracy and reliability, further improvements have been sought. Specifically, the use of such flow sensors in respiratory therapy equipment, particularly medical ventilators, has led to their fabrication from materials, such as stainless steel, that can be sterilized in autoclaves. A flapper made of stainless steel, however, is susceptible to fatigue and failure (especially at its hinged attachment point) due to repeated deflections over long periods of use, and due to overstress in response to high flow rates. This problem could be overcome by strengthening the hinged attachment part of the flapper and by increasing the area of the flapper so that it is not overstressed at high flow rates, but this solution would result in a loss of resolution at low flow rates.

Furthermore, it has been found that the use of stainless steel flappers has, in itself, resulted in the loss of low-end resolution. This is because, during the fabrication process, the stainless steel sheet takes a "set" that results in a flapper that deviates somewhat from a true planar configuration. In other words, the flapper is often slightly curved, so that, when it is installed in the orifice, there is a gap between the flapper's peripheral edge and the annular surface that defines the orifice. This results in a non-zero orifice area at zero flow rate, which, in turn, results in the loss of resolution at low flow rates. Furthermore, to avoid deterioration in accuracy due to exposure to the high temperatures of an autoclave, the flapper is advantageously annealed. The annealing process, however, softens the stainless steel, and the resultant loss of stiffness or rigidity causes the flapper to lose a measurable degree of responsiveness, most noticeable at low flow rates. Thus, the annealing process, while addressing one cause of inaccuracy (high temperature exposure), introduces another cause (loss of flapper rigidity).

Thus, there has been a need for a variable orifice flow sensor with a metal (preferably stainless steel) flapper that is capable of withstanding repeated deflections over a long period of use without fatigue or failure, even with repeated exposure to high flow rates. There has been a further need for such a flow sensor that also yields good low end sensitivity and resolution. There has been a still further need for such a flow sensor that is capable of withstanding repeated autoclaving without deterioration of accuracy over time, and without sacrificing responsiveness.

SUMMARY OF THE INVENTION

Broadly, the present invention is a variable orifice flow sensor, of the type comprising a first fluid flow port, a second fluid flow port, a flow conduit member defining a flow orifice and fluidly connecting the first and second fluid flow ports, a flapper of magnetizable sheet metal that is mounted in the conduit member by a hinge portion so that the flapper angularly deflects out of the plane of the orifice in response to fluid flow through the conduit member to vary the effective fluid flow cross-sectional area of the orifice in proportion to the flow rate of fluid through the conduit member, and a pressure sensing tap on either side of the flapper, wherein the improvement comprises a deflection-limiting surface in the conduit member adjacent the hinge portion against which the hinge portion abuts when the flapper experiences an angular deflection at least equal to a predefined angle in response to a fluid flow rate that is at least equal to a predetermined value, whereby overstressing of the hinge portion is minimized. The improvement further comprises at least one magnet in the conduit member adjacent to the flapper, whereby the magnet generates a magnetic field that acts on the flapper so as to force it into a position that tends to minimize the zero flow gap that exists between the flapper and the portion of the conduit member that defines the fluid flow orifice when there is no fluid flow through the orifice.

In a specific preferred embodiment, the hinge portion of the flapper is attached to a pivot member, such as a pin, a rivet, or an equivalent element. The pivot member has an axis that is substantially parallel to the axis of the conduit member. Extending radially inwardly into the conduit from the pivot member is a pair of support plates separated by an angled notch. The notch has an apex along a line that is perpendicular to the axis of the pivot member, so that the notch defines a pair of opposed deflection-limiting surfaces on the respective support plates that angle away from each other as they extend radially inwardly from the pivot member. The deflection-limiting surfaces of the plates thus define angular limits of travel for the hinge portion of the flapper.

Also, in the specific preferred embodiment, first and second disc-shaped magnets are respectively contained in first and second recesses formed in the exterior wall of the conduit member adjacent the flapper. The flapper is cut, stamped, or chemically etched from a sheet of stainless steel that is cold rolled to give it good magnetic properties. The location and the field strength of the magnets are selected so that the magnet field they create forces or pulls the flapper into a position in which the gap that exists between the edge of the flapper and the orifice-defining portion of the conduit member is minimized at zero flow conditions. The field strength is strong enough to simulate and thus compensate for the stiffness or rigidity that is lost during the annealing process (as discussed above), but not so strong, however, as to create a significant bias on the flapper at higher flow rates. Thus, low end responsiveness is improved without sacrificing high end accuracy.

As will be better appreciated from the detailed description that follows, the present invention offers significant advantages over the prior art. Specifically, the deflection-limiting surfaces limit the angular flexing of the hinge portion of the flapper, so that once the angular limits of travel are reached, the hinge portion undergoes little or no increase in stress. Rather, the flapper resiliently bends over the edges of the support plates at high flow rates, thereby yielding a measurement without significantly causing stress-induced fatigue in the hinge portion. This increases the useful lifetime of the sensor, even when it is subjected to high flow rates, without significantly affecting low flow rate resolution or sensitivity. Furthermore, the gap minimization created by the magnet or magnets enhances resolution at low flow rates. Thus, the sensor according to the present invention yields high lifetime and good resolution at both the high and low extremes of the flow rate range to be measured.

DETAILED DESCRIPTION OF A PREFERRED EMBODIMENT

Figure 1:
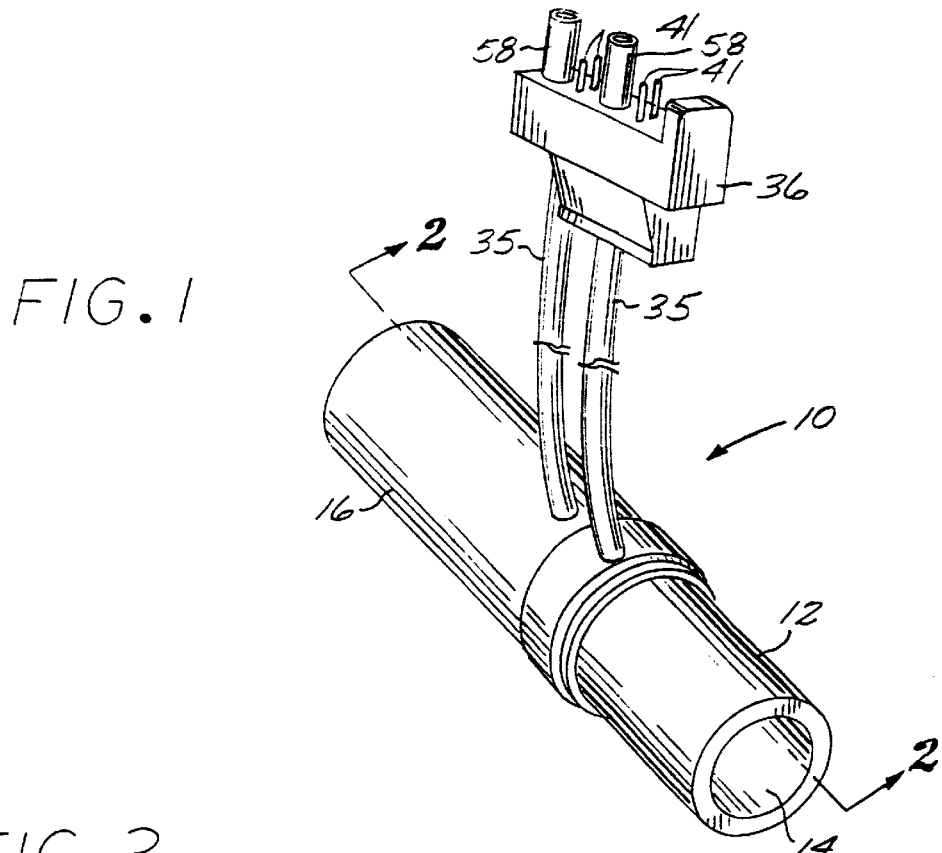
FIG. 1 is a perspective view of a fluid flow sensor in accordance with a preferred embodiment of the present invention.
Figure 2:
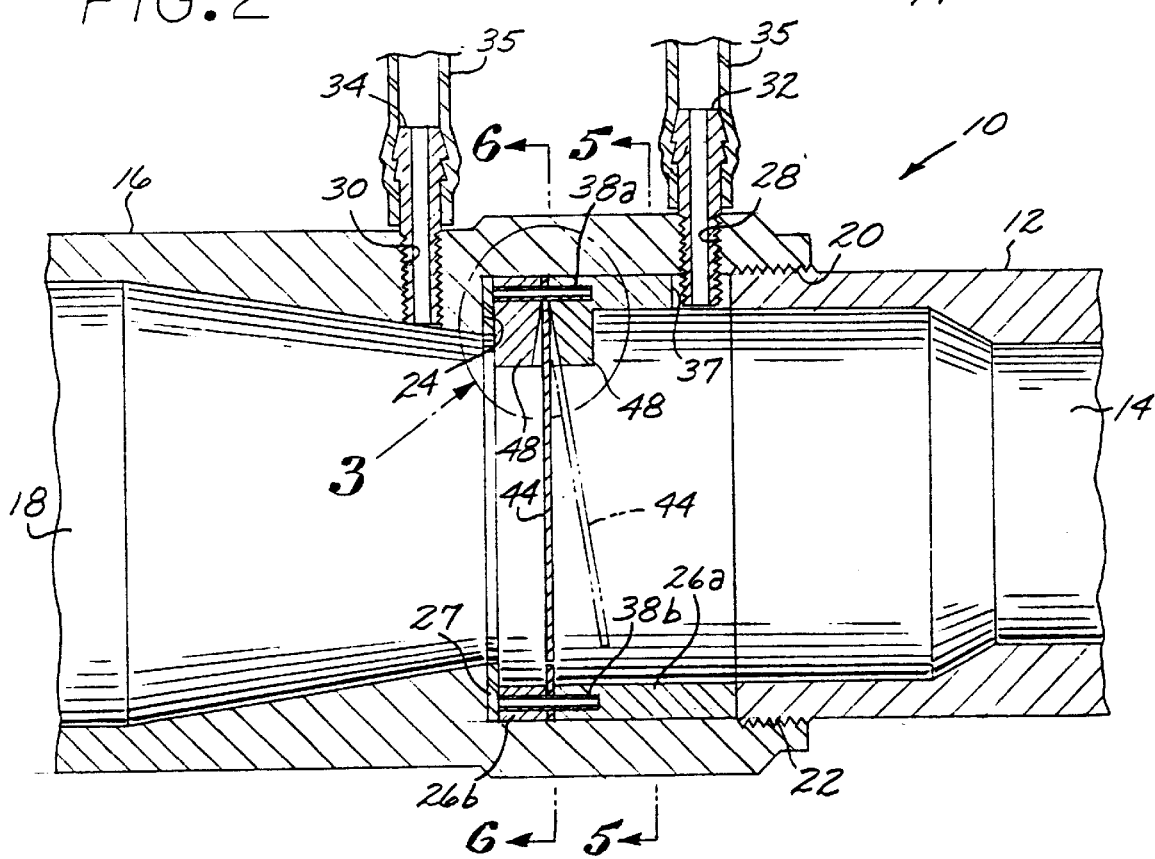
FIG. 2 is an axial cross-sectional view taken along line 2—2 of FIG. 1.

Referring now to FIGS. 1 through 8, a variable orifice fluid flow sensor 10, in accordance with a preferred embodiment of the invention, is shown. As best shown in FIGS. 1 and 2, the sensor 10 comprises a first tubular member 12 that defines a first fluid flow port 14 and a second tubular member 16 that defines a second fluid flow port 18. The second tubular member 16 has an internally-threaded opening 20 opposite the second fluid flow port 18 that receives an externally-threaded end 22 of the first tubular member 12. Thus, the first and second tubular members 12, 16 may be detachably coupled to each other by the mating screw threads of the threaded opening 20 and the threaded end 22. Because the sensor 10 is a bidirectional sensor, each of the fluid flow ports 14, 18 may function as either an input port or an output port.

Figure 10:
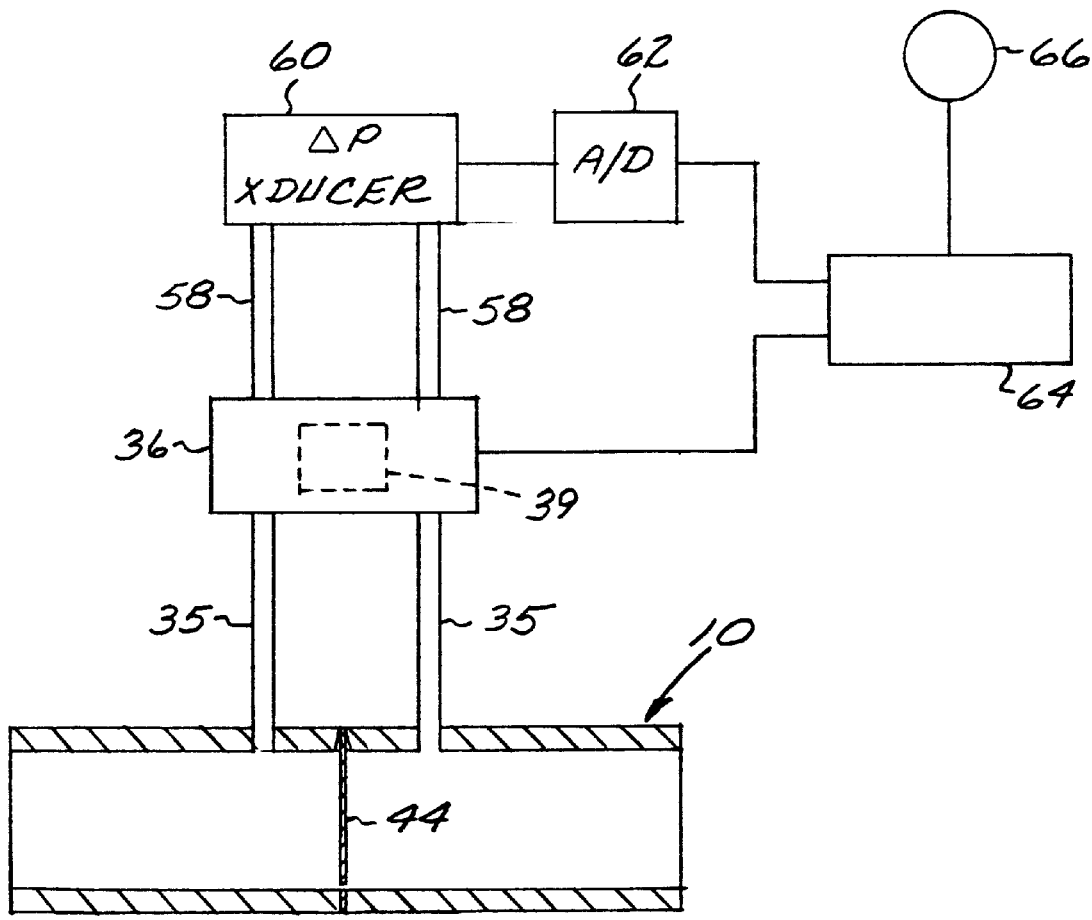
FIG. 10 is a schematic representation of a flow rate measuring system incorporating a flow sensor in accordance with the present invention.

Formed inside the second tubular member 16 a short distance inwardly from the threaded opening 20 is an annular shoulder 24. The shoulder 24 forms a seat for a short tubular conduit member 26, to be described more fully below. An annular washer 27 may advantageously be provided between the shoulder 24 and the conduit member 26. The second tubular member 16 is provided with a first internally-threaded radial bore 28 just inwardly from the threaded opening 20. A second internally-threaded radial bore 30 is provided in the second tubular member 16 a short distance inwardly from the shoulder 24, on the opposite side thereof from the first radial bore 28. The first and second radial bores 28, 30 respectively receive first and second pressure sensing taps 32, 34, each of which has an externally threaded portion that mates with the internal threads of its respective radial bore. The pressure sensing taps 32, 34 are respectively connected, by flexible conduits 35, to the input side of an electronic module 36, which contains an electrically-erasable programmable read-only memory (EEPROM) chip 39 (FIG. 10). The module 36 is made of an autoclavable plastic, and the EEPROM 39 is potted in a heat-resistant epoxy, so that the entire module 36 may be sterilized in an autoclave along with the sensor 10. The module 36 includes a plurality of conductive pins 41, as shown in FIG. 1, that are electrically connected to appropriate input and output terminals (not shown) in the EEPROM 39, so that data can be stored in and retrieved from the EEPROM 39, as described below.

The conduit member 26 is preferably formed of a corrosion-resistant, nonmagnetic material, such as aluminum or an autoclavable plastic. It provides fluid communication between the first and second fluid flow ports 14, 18. The conduit member 26 has an outside diameter that is slightly smaller than the inside diameter of the threaded opening, so that it can be inserted through the threaded opening 20 into the second tubular member 16 until it seats against the washer 27. The edge of the conduit member 26 facing the first tubular member 12 includes a notch or cut-out 37 that registers with the first radial bore 28 in the second tubular member 16, and that receives the first pressure sensing tap 32. To install or remove the conduit member 26, the first pressure sensing tap 32 must be at least partially withdrawn from the first radial bore 28 a sufficient distance to provide clearance for the conduit member 26.

Figure 6:
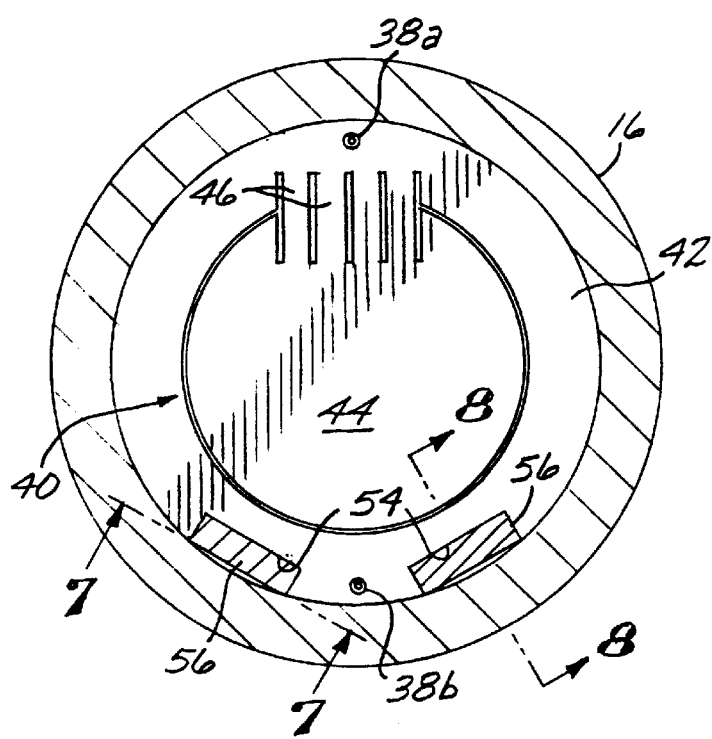
FIG. 6 is a cross-sectional view taken along line 6—6 of FIG. 2.

The conduit member 26 is formed from a pair of rings 26a, 26b that are attached in tandem to each other at diametrically opposite points by first and second attachment pins 38a, 38b, respectively. Alternatively, rivets, rods, screws, or equivalent attachment means (such as adhesives) can be used to attach the rings 26a, 26b together to form the conduit member 26. Captured between the rings 26a, 26b is a thin diaphragm 40 that is cut, stamped, or chemically etched from a sheet of stainless steel that is cold rolled to give it good magnetic properties. As best shown in FIG. 6, the diaphragm 40 comprises a fixed outer annular portion 42 that is captured between the rings 26a, 26b and is fixed thereto by the pins 38a, 38b. The annular portion 42 thus becomes the portion of the conduit member 26 that defines the fluid flow orifice of the sensor 10. The central portion of the diaphragm 40 is formed as a flow responsive flapper 44 that variably obstructs a fluid flow orifice defined by the outer annular portion 42 of the diaphragm 40. The flapper 44 is connected to the outer annular portion 42 by a hinge portion 46, so that the flapper 44 may undergo an angular deflection, in either direction, with respect to the plane of the fluid flow orifice, i.e., the plane defined by the outer annular portion 42. The effective fluid flow cross-sectional area of the fluid flow orifice is proportional to the angular deflection of the flapper 44, as will be described below.

Figure 3:
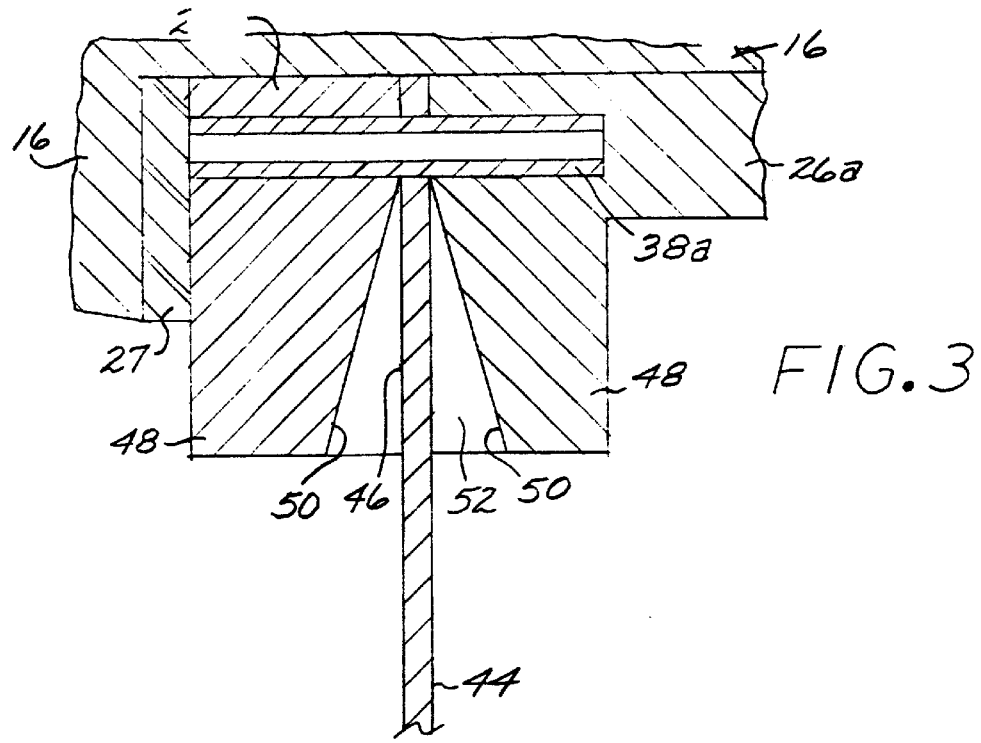
FIG. 3 is a detailed view taken within the area defined within the broken outline 3 of FIG. 2, showing the flapper in a zero flow position.
Figure 4:
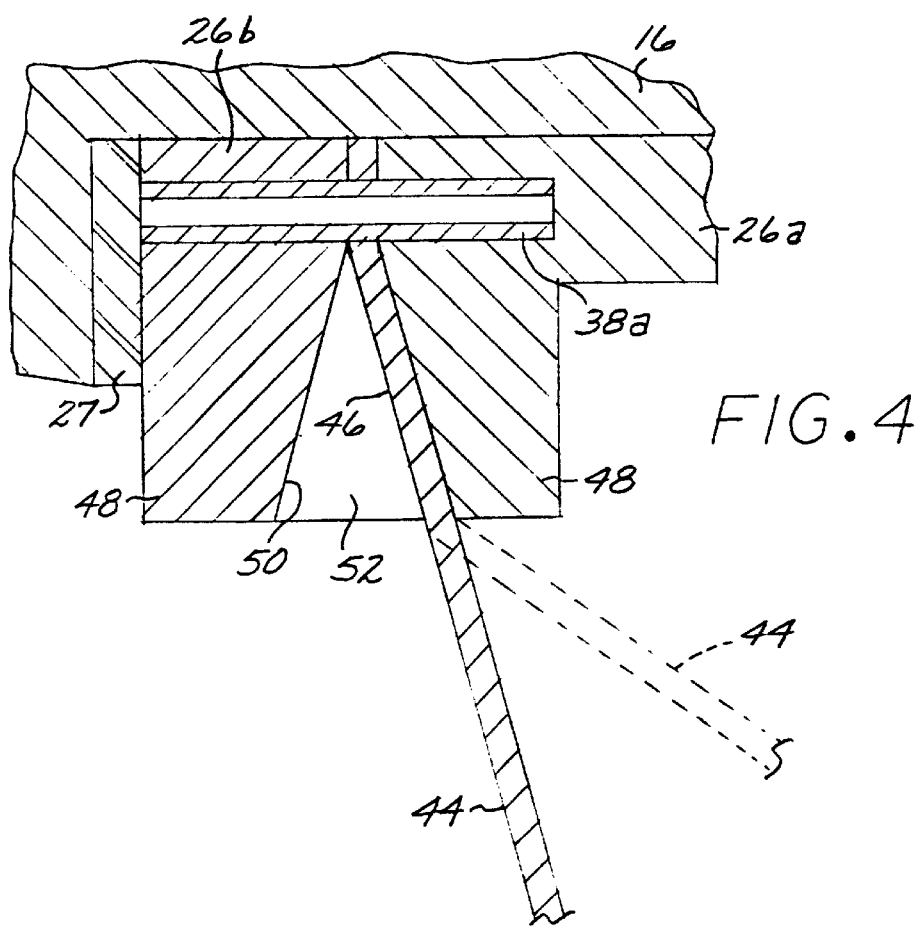
FIG. 4 is a view similar to that of FIG. 3, but showing the flapper at one angular extreme of travel in response to a high fluid flow rate.
Figure 5:
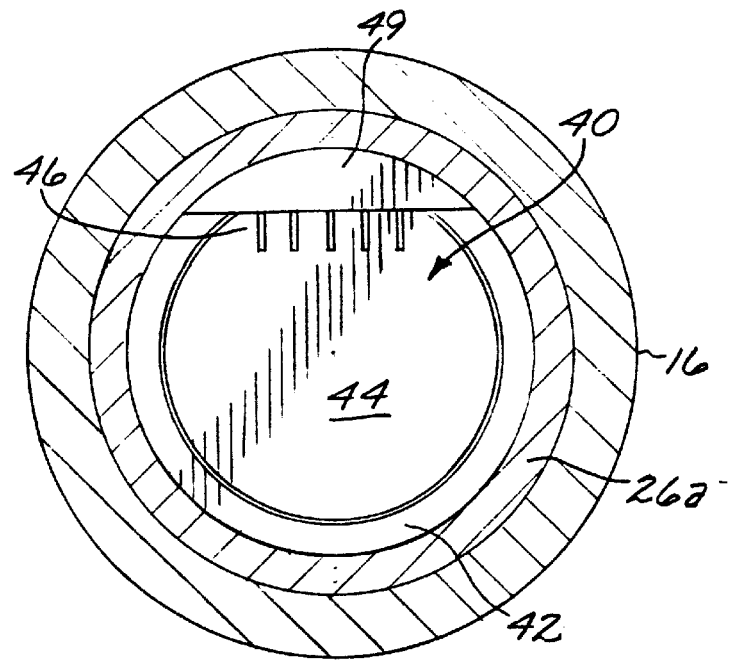
FIG. 5 is a cross-sectional view taken along line 5—5 of FIG. 2.

As best shown in FIGS. 3 and 4, the hinge portion 46 of the flapper 44 is connected to the conduit member 26 by the first attachment pin 38a, which thus functions as a pivot member. Below the first attachment pin 38a, each of the rings 26a, 26b is formed with a downward-depending plate 48 that includes a deflection-limiting surface 50. The deflection-limiting surfaces 50 angle away from each other to form an angled notch 52 having an apex along a line that is perpendicular to the axis of the first attachment pin 38a. In a specific preferred embodiment, the notch subtends an angle of approximately 30 degrees. The purpose of the deflection-limiting surfaces 50 will be explained below.

Figure 7:
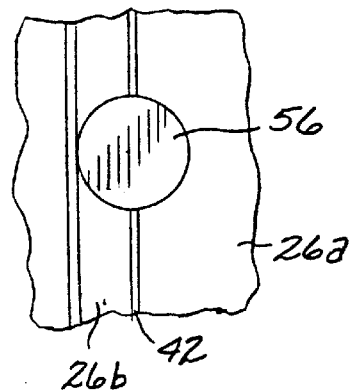
FIG. 7 is a cross-sectional view taken along line 7—7 of FIG. 6.
Figure 8:
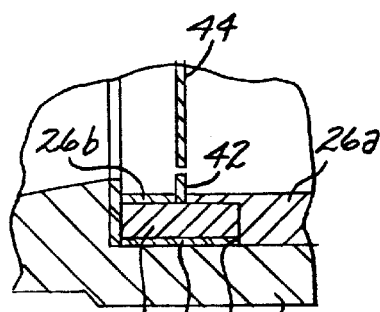
FIG. 8 is a cross-sectional view taken along line 8—8 of FIG. 7.

Referring to FIGS. 6, 7, and 8, the outer wall surface of the conduit member 26 is formed with a pair of shallow pockets 54 on either side of the lower attachment pin 38b. The pockets 54 are located at the juncture between the rings 26a, 26b, where the outer annular portion 42 of the diaphragm 40 is captured. Accordingly, the annular portion 42 of the diaphragm 40 includes a pair of recesses that register with the pockets 54, so that the pockets 54 are formed in the rings 26a, 26b and in the annular portion 42 of the diaphragm 40. Each pocket 54 receives a disc-shaped permanent magnet 56. The magnets 56 are attracted to the diaphragm 40, and they are sealed in place by a liquid silicone rubber adhesive sealant 57 (FIG. 8), that hardens quickly upon exposure to the ambient atmosphere at room temperature. If the sensor is used in a a medical application (e.g., a medical ventilator), the sealant should conform to the FDA regulation set forth at 21 CFR 177.2600. A suitable material that conforms to this regulation is marketed by General Electric Company, of Waterford, N.Y., under the proprietary name "RTV 110". The sealant 57 not only holds the magnets 56 in the pockets 54, it also protects them from corrosion.

The operation of the sensor 10 may now be described. At zero fluid flow rate through the conduit member 26 (in either direction), a static flow condition is defined. The plane of the flapper 44 is substantially perpendicular to the fluid flow path, which is along the longitudinal axis of the tubular members 12, 16 and the conduit member 26. The gap between the flapper 44 and outer annular portion 42 of the diaphragm 40 is at a minimum (e.g., less than 1 mm in adult medical ventilator applications), so that the effective fluid flow cross-sectional area of the flow orifice defined by the annular portion 42 is minimized. Since there is no flow across the fluid flow orifice, the pressure drop between the pressure taps 32, 34 is zero.

At non-zero fluid flow rates, the flapper is deflected angularly out of the plane of the fluid flow orifice. The angle of deflection is proportional to the fluid flow rate, and the effective fluid flow cross-sectional area of the fluid flow orifice is proportional to the angle of deflection. Thus, the effective fluid flow cross-sectional area of the fluid flow orifice increases proportionately with the flow rate through the orifice.

The pressure drop of a fluid flowing through a fixed orifice is proportional to the square of the flow rate. In the present invention, because the cross-sectional area of the orifice increases substantially linearly with the flow rate, the pressure drop is a more nearly linear function of the flow rate. One consequence of this phenomenon is that the pressure drop at low flow rates is increased in comparison to that experienced across a fixed orifice, while the pressure drop at high flow rates is decreased, as compared with a fixed orifice flow sensor.

As shown in FIG. 10, the pressure drop across the orifice is sensed by the pressure taps 32, 34, and communicated, via the flexible tubes 35, to the input side of the module 36. The module 36 includes a pair of internal passages (not shown) that communicate the sensed pressure drop to a corresponding pair of outlet ports 58 (FIG. 1), which are connectable by means of flexible tubing (not shown) to a differential pressure transducer 60, of any suitable type well-known in the art. The pressure transducer 60 generates an analog electrical signal having a value indicative of the pressure drop. This analog signal is digitized by an analog-to-digital converter 62 (of any suitable type well-known in the art) and input to a microcomputer 64 that is programmed to generate a value representing the instantaneous volumetric flow rate through the orifice. The programming required to perform this function is a routine matter to those skilled in the pertinent arts. For example, an empirically-derived look-up table of flow rate versus pressure values can be stored in the EEPROM 39 that is addressed by the microcomputer 64 at prescribed intervals. The instantaneous volumetric flow rate value generated by the microcomputer 64 is then output to display device 66, which may be a meter or an alphanumeric display (e.g., LED, LCD, or gas discharge display).

The look-up table stored in the EEPROM 39 may be generated by a prior calibration of the flow sensor, by known calibration techniques. For example, a variable air flow source may be used that generates known flow rates of precise values throughout the intended range of the sensor 10.

Low flow rate resolution and sensitivity depend on the gap between the flapper 44 and the orifice-defining annular portion 42 being minimized. Typically, a gap of no more than about one millimeter (preferably slightly less) is desired. Due to limitations in the fabrication of the stainless steel diaphragm 40, the diaphragm 40, including the flapper 44, often deviates from a strictly planar configuration. This deviation creates a gap that can vary from sensor to sensor, and that can be significantly larger than the desired one millimeter maximum value.

To overcome this problem, the magnets 56 are employed. The magnets 56 are configured and located so that the magnetic fields they generate pull the flapper 44 into a position in which the gap between the flapper and the annular portion 42 is minimized. The magnetic field strength is strong enough to simulate and thus compensate for the stiffness or rigidity that is lost during the annealing process, but not so strong, however, as to create a significant bias on the flapper at higher flow rates. Within these constraints, the field strength is selected so that the threshold flow rate needed to deflect the flapper 44 is kept to an acceptable minimum (typically less than 1 LPM).

Figure 9:
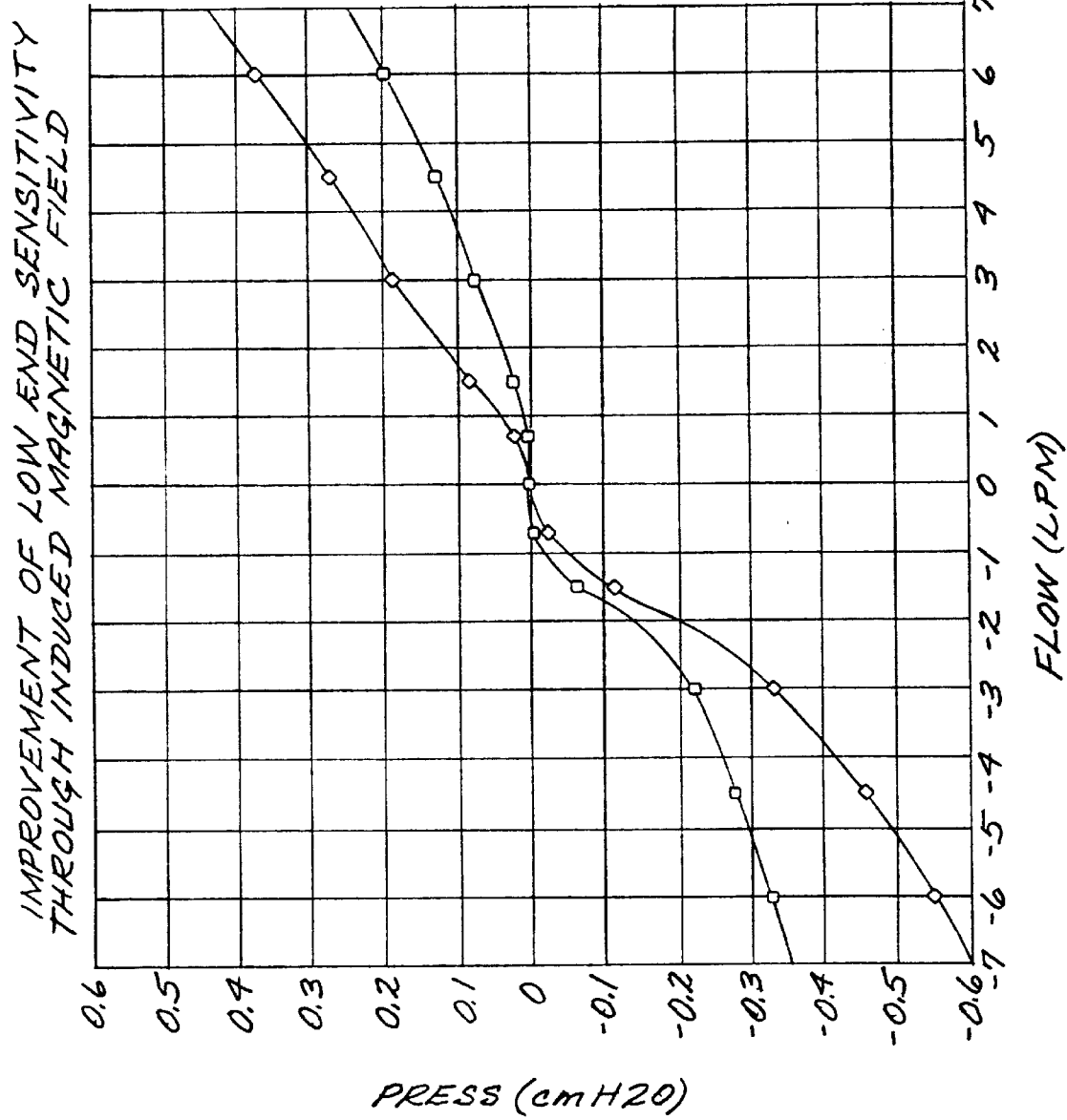
FIG. 9 is a graph of pressure drop across the flow orifice as a function of flow rate, comparing the performance of the sensor at low flow rates with and without the improvement provided by the magnet or magnets of the present invention.

FIG. 9 illustrates the improved low-end performance of a flow sensor that incorporates the above described improvement as compared with a prior art flow sensor that lacks the magnets 56. FIG. 9 is a graph of measured pressure drop versus flow rate over a range of −7 LPM to +7 LPM (indicating bidirectional flow). In FIG. 9, curve A, defined by square data points, represents pressure drop measurements as a function of flow rate for a prior art flow sensor lacking the magnets 56, while curve B, defined by diamond-shaped data points, represents pressure drop measurements as a function of flow rate for the improved flow sensor employing the magnets 56. A comparison of curves A and B shows enhanced sensitivity (i.e., greater absolute values of the pressure drop as a function of flow rate) at low flow rates for the improved sensor in accordance with the present invention. From this enhanced sensitivity follows enhanced resolution, at low flow rates, of the improved flow sensor with the magnets 56.

In a specific prototype of the invention, calibrated flow rates as low as ±0.7 liters per minute (LPM) were employed, and compared to similar flow rates through a flow sensor identical to the subject invention, but lacking the magnets 56. In the invention prototype, the pressure drop at −0.7 LPM was approximately −0.026 centimeters of water ($cmH_2O$), and at +0.7 LPM it was approximately 0.0188 $cmH_2O$. This compares favorably to the unimproved sensor, which had a pressure drop at −0.7 LPM of approximately −0.008 $cmH_2O$ and at +0.7 LPM of approximately 0.002 $cmH_2O$.

While it has been found that two disc-shaped magnets 56, located equidistantly from the second attachment pin 38b (as shown in FIG. 6) yields optimal results and provides ease of assembly (in that the location of the second attachment pin 38b does not have to be changed), other magnet configurations and locations may yield acceptable results. For example, by moving (or eliminating) the second attachment pin 38b, a single magnet may be used to good effect.

FIG. 4 illustrates the action of the flapper 44 at high flow rates. Up to a predetermined flow rate, the entire flapper 44 is deflected at a uniform angle, pivoting about the upper attachment pin 38a by means of the hinge portion 46. At this point, further pivoting of the hinge portion 46 is limited by its abutment against one of the deflection-limiting surfaces 50, as shown in solid outline in FIG. 4. At flow rates greater than the predetermined flow rate, the flapper 44 resiliently ends around the bottom of the adjacent abutment plate 48, as shown in broken outline in FIG. 4. This bending action allows the flapper to continue its function of increasing the effective fluid flow cross-sectional area of the orifice, without placing additional stress on the relatively delicate hinge portion 46. This allows higher flow rates to be measured without deforming or damaging the hinge portion 46 than has heretofore been possible, while also increasing the cyclic lifetime of the sensor.

As mentioned above, the angle subtended by the notch 52 in a specific preferred embodiment of the invention is 30°. Thus, the maximum angular deflection of the hinge portion 46 in either direction is one-half the angle subtended by the notch 52, i.e., 15° for the exemplary embodiment described herein. For any given fluid flow range to be measured by the sensor 10, and/or for any given fluid flow cross-sectional area of the orifice obstructed by the flapper 44 (which may be related to the fluid flow range to be measured), there will be a very small range of notch angles that will provide acceptable performance. If the notch angle is too large, the hinge portion 46 will undergo excessive flexing, resulting in potential premature failure. If the angle is too small, the resistance of the flapper 44 due to the constraints on the movement of the hinge portion 46 may generate excessively high pressure drops at high flow rates. Excessively high pressure drops are to be avoided in applications such as medical ventilators, because they may be experienced as a back pressure than can interfere with a patient's breathing. In a prototype of the invention, designed to measure flow rates up to about 100 LPM, and with a fluid flow orifice diameter (flapper diameter) of about 16 mm, the 30° angle specified above yields optimum results. This angle may need to be changed if either higher maximum flow rates (e.g., up to about 900 LPM) or lower maximum flow rates (e.g., down to about 30 LPM) are to be measured.

It will thus be appreciated that the present invention offers significant advantages over the prior art. Specifically, the angled deflection-limiting surfaces 50 limit the angular flexing of the hinge portion 46 of the flapper 44, so that once the angular limits of travel are reached, the hinge portion 46 undergoes little or no increase in stress. Rather, the flapper 44 resiliently bends over the edges of the support plates 48 at high flow rates, thereby yielding a measurement without significantly causing stress-induced fatigue in the hinge portion 46. This increases the useful lifetime of the sensor, even when it is subjected to high flow rates, without significantly affecting low flow rate resolution or sensitivity. Furthermore, the gap minimization created by the magnets 56 enhances resolution at low flow rates. Thus, the sensor according to the present invention yields high lifetime and good resolution at both the high and low extremes of the flow rate range to be measured.

While a preferred embodiment of the invention has been described herein, it will be appreciated that a number of modifications and variations may suggest themselves to those skilled in the pertinent arts. For example, the configuration of the diaphragm member 40, including the orifice-defining annular portion 42, the hinge portion 46, and the flapper 44 may assume a variety of configurations, some of which are suggested in the aforementioned U.S. Pat. No. 4,993,269. The configuration and dimensions of the diaphragm member 40 may be dictated by the application of the sensor 10, including such considerations as the expected flow rate range to be measured, the degree of sensitivity and resolution desired, and the desired lifetime (in terms of expected full or nearly full angular excursions of the flapper). Thus, the embodiment described herein should be considered exemplary only, and the variations and modifications that may suggest themselves should be considered within the spirit and scope of the invention, as defined in the claims that follow.

What is claimed is:

1. A variable orifice flow sensor, of the type including a flow conduit member defining a flow orifice and fluidly connecting first and second fluid flow ports, a flapper with a pressure sensing tap on either side thereof, said flapper made of a magnetizable metal and mounted in the conduit member by a hinge portion so that the flapper angularly deflects out of the plane of the orifice in response to fluid flow through the conduit member to vary the effective fluid flow cross-sectional area of the orifice in proportion to the flow rate of fluid through the conduit member, and wherein a zero flow gap is defined between the flapper and the conduit member when there is no fluid flow through the orifice, wherein the improvement comprises:

a) a deflection-limiting surface in the conduit member adjacent the hinge portion against which the hinge portion abuts when the flapper experiences an angular deflection at least equal to a predefined angle in response to a fluid flow rate that is at least equal to a predetermined value; and b) a magnetic element in the conduit member adjacent the flapper, the magnetic element being located and configured so as to generate a magnetic field that forces the flapper into a position that tends to minimize the zero flow gap.

2. The flow sensor of claim 1, wherein the magnetic field is selected so that the threshold flow rate needed to deflect the flapper is less than a predetermined minimum flow rate.

3. The flow sensor of claim 1, wherein the magnetic element comprises a pair of permanent magnets.

4. The flow sensor of claim 1, wherein the conduit member includes an outer wall surface in which is formed a pocket, and wherein the magnetic element includes a permament magnet retained in the pocket.

5. The flow sensor of claim 1, wherein the conduit member includes an outer wall surface in which is formed a pair of pockets, and wherein the magnetic element comprises a permanent magnet retained in each of the pockets.

6. A variable orifice flow sensor, of the type including a flow conduit member defining a flow orifice and fluidly connecting first and second fluid flow ports, a magnetizable metal flapper that is mounted in the conduit member by a hinge portion so that a zero-flow gap is defined between the flapper and the conduit member when there is no fluid flow through the orifice and so that the flapper angularly deflects out of the plane of the orifice in response to fluid flow through the conduit member to vary the effective fluid flow cross-sectional area of the orifice in proportion to the flow rate of fluid through the conduit member, and a pressure sensing tap on either side of the flapper, wherein the improvement comprises:

a magnetic element in the conduit member adjacent the flapper, the magnetic element being located and configured so as to generate a magnetic field that forces the flapper into a position that tends to minimize the zero flow gap.

7. The flow sensor of claim 6, wherein the magnetic field is selected so that the threshold flow rate needed to deflect the flapper is less than a predetermined minimum flow rate.

8. The flow sensor of claim 6, wherein the magnetic element comprises a pair of permanent magnets.

9. The flow sensor of claim 6, wherein the conduit member includes an outer wall surface in which is formed a pocket, and wherein the magnetic element includes a permament magnet retained in the pocket.

10. The flow sensor of claim 6, wherein the conduit member includes an outer wall surface in which is formed a pair of pockets, and wherein the magnetic element comprises a permanent magnet retained in each of the pockets.

11. The flow sensor of claims 6, 7, 8, 9, or 10, wherein the improvement further comprises:

a deflection-limiting surface in the conduit member adjacent the hinge portion against which the hinge portion abuts when the flapper experiences an angular deflection at least equal to a predefined angle in response to a fluid flow rate that is at least equal to a predetermined value.

12. The flow sensor of claim 11, wherein the deflection-limiting surface is defined by a support plate depending from the conduit member adjacent the hinge portion.

13. The flow sensor of claim 12, wherein the deflection-limiting surface comprises a pair of deflection-limiting surfaces defined by a pair of support plates depending from the conduit member adjacent the hinge portion, the deflection-limiting surfaces being separated by an angled notch.

14. The flow sensor of claim 13, wherein the hinge portion is connected to the conduit member by a pivot member having an axial dimension, and wherein the notch has an apex along a line that is perpendicular to the axial dimension of the pivot member.

15. A variable orifice flow sensor, of the type including a flow conduit member defining a flow orifice and fluidly connecting first and second fluid flow ports, a flapper that is mounted in the conduit member by a hinge portion so that the flapper angularly deflects out of the plane of the orifice in response to fluid flow through the conduit member to vary the effective fluid flow cross-sectional area of the orifice in proportion to the flow rate of fluid through the conduit member, and a pressure sensing tap on either side of the flapper, wherein the improvement comprises:

a deflection-limiting surface in the conduit member adjacent the hinge portion against which the hinge portion abuts when the flapper experiences an angular deflection at least equal to a predefined angle in response to a fluid flow rate that is at least equal to a predetermined value, and further wherein a zero flow gap is defined between the flapper and the conduit member when there is no fluid flow through the orifice, wherein the flapper is made of a magnetizable metal, and wherein a magnetic element in the conduit member is adjacent the flapper, the magnetic element being located and configured so as to generate a magnetic field that forces the flapper into a position that tends to minimize the zero flow gap.

16. The flow sensor of claim 15, wherein the magnetic field is selected so that the threshold flow rate needed to deflect the flapper is less than a predetermined minimum flow rate.

17. The flow sensor of claim 15, wherein the magnetic element comprises a pair of permanent magnets.

18. The flow sensor of claim 15, wherein the conduit member includes an outer wall surface in which is formed a pocket, and wherein the magnetic element includes a permanent magnet retained in the pocket.

19. The flow sensor of claim 15, wherein the conduit member includes an outer wall surface in which is formed a pair of pockets, and wherein the magnetic element comprises a permanent magnet retained in each of the pockets.

20. A variable orifice flow sensor, of the type including a flow conduit member defining a flow orifice and fluidly connecting first and second fluid flow ports, a flapper that is mounted in the conduit member by a hinge portion so that the flapper angularly deflects out of the plane of the orifice in response to fluid flow through the conduit member to vary the effective fluid flow cross-sectional area of the orifice in proportion to the flow rate of fluid through the conduit member, and a pressure sensing tap on either side of the flapper, wherein the improvement comprises:

a deflection-limiting surface in the conduit member defined by a support plate depending from the conduit member adjacent the hinge portion against which the hinge portion abuts when the flapper experiences an angular deflection at least equal to a predefined angle in response to a fluid flow rate that is at least equal to a predetermined value, and further wherein a zero flow gap is defined between the flapper and the conduit member when there is no fluid flow through the orifice, wherein the flapper is made of a magnetizable metal, and wherein a magnetic element in the conduit member is adjacent the flapper, the magnetic element being located and configured so as to generate a magnetic field that forces the flapper into a position that tends to minimize the zero flow gap.

21. The flow sensor of claim 20, wherein the magnetic field is selected so that the threshold flow rate needed to deflect the flapper is less than a predetermined minimum flow rate.

22. The flow sensor of claim 20, wherein the magnetic element comprises a pair of permanent magnets.

23. The flow sensor of claim 20, wherein the conduit member includes an outer wall surface in which is formed a pocket, and wherein the magnetic element includes a permanent magnet retained in the pocket.

24. The flow sensor of claim 20, wherein the conduit member includes an outer wall surface in which is formed a pair of pockets, and wherein the magnetic element comprises a permanent magnet retained in each of the pockets.

25. A variable orifice flow sensor, of the type including a flow conduit member defining a flow orifice and fluidly connecting first and second fluid flow ports, a flapper that is mounted in the conduit member by a hinge portion so that the flapper angularly deflects out of the plane of the orifice in response to fluid flow through the conduit member to vary the effective fluid flow cross-sectional area of the orifice in proportion to the flow rate of fluid through the conduit member, and a pressure sensing tap on either side of the flapper, wherein the improvement comprises:

a deflection-limiting surface in the conduit member adjacent the hinge portion against which the hinge portion abuts when the flapper experiences an angular deflection at least equal to a predefined angle in response to a fluid flow rate that is at least equal to a predetermined value, with said deflection-limiting surface defined by a support plate depending from the conduit member adjacent the hinge portion and comprising a pair of deflection-limiting surfaces defined by a pair of support plates depending from the conduit member adjacent the hinge portion and being separated by an angled notch, and further wherein a zero flow gap is defined between the flapper and the conduit member when there is no fluid flow through the orifice, wherein the flapper is made of a magnetizable metal, and wherein a magnetic element in the conduit member is adjacent the flapper, the magnetic element being located and configured so as to generate a magnetic field that forces the flapper into a position that tends to minimize the zero flow gap.

26. The flow sensor of claim 25, wherein the magnetic field is selected so that the threshold flow rate needed to deflect the flapper is less than a predetermined minimum flow rate.

27. The flow sensor of claim 25, wherein the magnetic element comprises a pair of permanent magnets.

28. The flow sensor of claim 25, wherein the conduit member includes an outer wall surface in which is formed a pocket, and wherein the magnetic element includes a permanent magnet retained in the pocket.

29. The flow sensor of claim 25, wherein the conduit member includes an outer wall surface in which is formed a pair of pockets, and wherein the magnetic element comprises a permanent magnet retained in each of the pockets.

30. A variable orifice flow sensor, of the type including a flow conduit member defining a flow orifice and fluidly connecting first and second fluid flow ports, a flapper that is mounted in the conduit member by a hinge portion so that the flapper angularly deflects out of the plane of the orifice in response to fluid flow through the conduit member to vary the effective fluid flow cross-sectional area of the orifice in proportion to the flow rate of fluid through the conduit member, and a pressure sensing tap on either side of the flapper, wherein the improvement comprises:

a deflection-limiting surface in the conduit member adjacent the hinge portion against which the hinge portion abuts when the flapper experiences an angular deflection at least equal to a predefined angle in response to a fluid flow rate that is at least equal to a predetermined value, with said deflection-limiting surface defined by a support plate depending from the conduit member adjacent the hinge portion and comprising a pair of deflection-limiting surfaces defined by a pair of support plates depending from the conduit member adjacent the hinge portion and being separated by an angled notch, and with the hinge portion connected to the conduit member by a pivot member having an axial dimension and wherein the notch has an apex along a line that is perpendicular to the axial dimension of the pivot member, and further wherein a zero flow gap is defined between the flapper and the conduit member when there is no fluid flow through the orifice, wherein the flapper is made of a magnetizable metal, and wherein a magnetic element in the conduit member is adjacent the flapper, the magnetic element being located and configured so as to generate a magnetic field that forces the flapper into a position that tends to minimize the zero flow gap.

31. The flow sensor of claim 30, wherein the magnetic field is selected so that the threshold flow rate needed to deflect the flapper is less than a predetermined minimum flow rate.

32. The flow sensor of claim 30, wherein the magnetic element comprises a pair of permanent magnets.

33. The flow sensor of claim 30, wherein the conduit member includes an outer wall surface in which is formed a pocket, and wherein the magnetic element includes a permanent magnet retained in the pocket.

34. The flow sensor of claim 30, wherein the conduit member includes an outer wall surface in which is formed a pair of pockets, and wherein the magnetic element comprises a permanent magnet retained in each of the pockets.

* * * * *